United States Patent [19]

Koyano et al.

[11] 4,002,577

[45] Jan. 11, 1977

[54] COPPER CARBONYL-CONTAINING CATALYTIC SOLUTIONS

[75] Inventors: Takashi Koyano, Tokyo; Yoshihisa Matsushima, Ohi; Tetsuo Kitamura, Kawasaki, all of Japan

[73] Assignee: Toa Nenryo Kogyo Kabushiki Kaisha, Tokyo, Japan

[22] Filed: Aug. 28, 1975

[21] Appl. No.: 609,538

Related U.S. Application Data

[63] Continuation of Ser. No. 385,156, Aug. 2, 1973, abandoned.

[30] Foreign Application Priority Data

| Aug. 7, 1972 | Japan | 47-78401 |
| Jan. 29, 1973 | Japan | 48-11144 |
| Feb. 27, 1973 | Japan | 48-22691 |

[52] U.S. Cl. .............. 252/433; 260/413; 260/514 M; 260/532; 260/533 A
[51] Int. Cl.² .......................... B01J 27/12
[58] Field of Search ................... 252/433

[56] References Cited

UNITED STATES PATENTS

| 1,914,785 | 6/1933 | Oxley | 252/437 X |
| 2,324,073 | 7/1943 | Gaylor et al. | 252/433 X |
| 3,099,687 | 7/1963 | Rohlffs et al. | 252/433 X |
| 3,262,954 | 7/1966 | Wehe et al. | 252/433 X |

*Primary Examiner*—Patrick P. Garvin
*Attorney, Agent, or Firm*—Rebecca Yablonsky

[57] ABSTRACT

A novel catalytic composition is described, useful for treating olefins or alcohols with carbon monoxide in the preparation of carboxylic acids comprising a solution containing copper carbonyl and a hydrated boron fluoride which optionally may contain a mineral acid such as sulfuric acid, phosphoric acid or hydrogen fluoride. The copper carbonyl functions as a cocatalyst for the hydrated boron trifluoride to enhance selectivity. The catalysts are especially suited for the preparation of neo acids.

7 Claims, 1 Drawing Figure

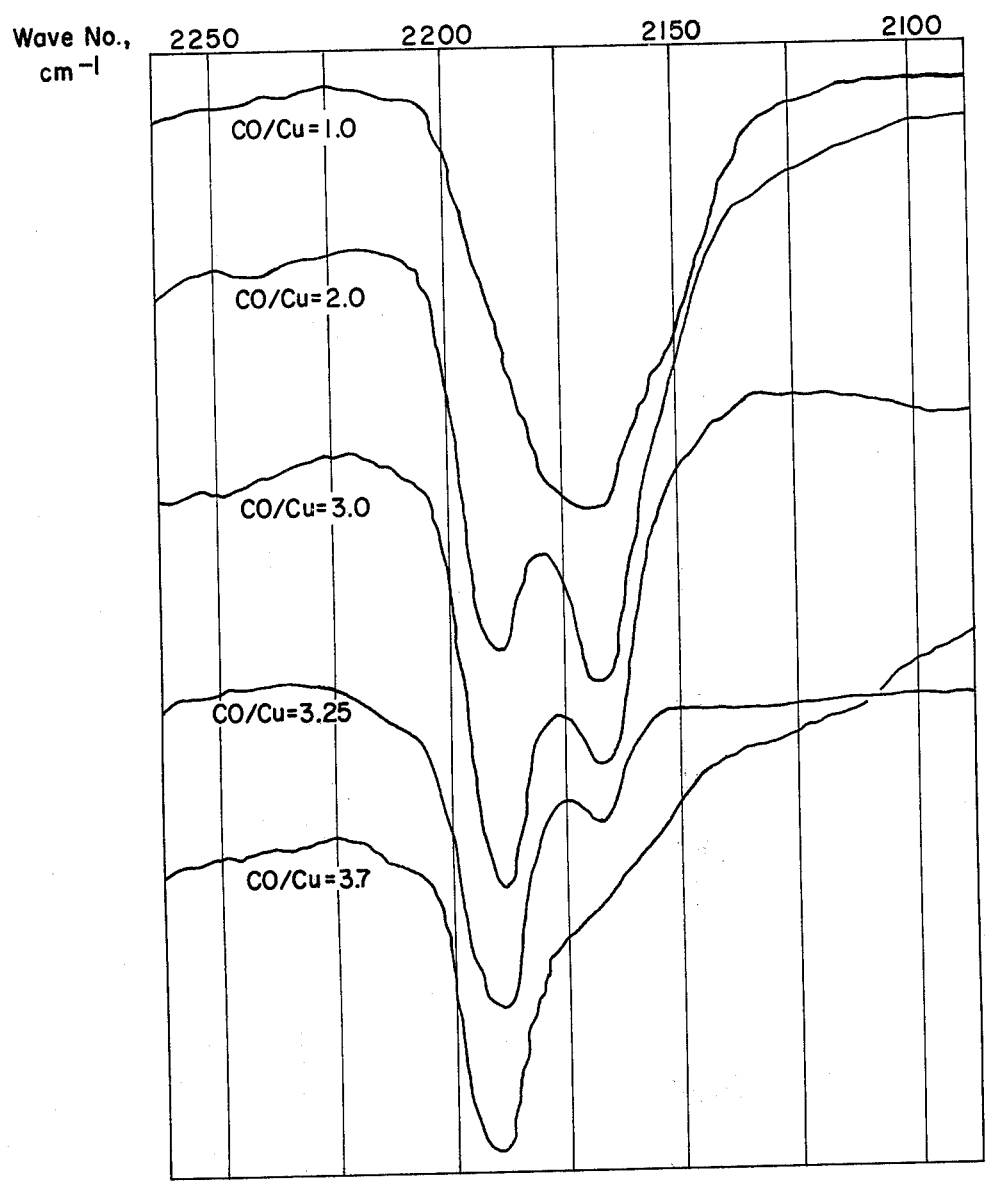

COPPER CARBONYL-CONTAINING CATALYTIC SOLUTIONS

This is a continuation of application Ser. No. 385,156, filed Aug. 2, 1973, now abandoned.

FIELD OF THE INVENTION

This invention relates to novel copper carbonylcontaining catalytic solutions, their preparation and use, particularly for treating olefins or alcohols with carbon monoxide in the preparation of carboxylic acids.

DESCRIPTION OF THE PRIOR ART

The production of carboxylic acids from olefins, carbon monoxide and water in the presence of a variety of acidic catalysts is well known, see U.S. Pat. No. 2,135,459 to Loder, issued on Nov. 1, 1938.

A process for producing a carboxylic acid containing a tertiary carbon atom attached to the carboxyl group, the so-called Koch process, is known in which an aliphatic or alicyclic olefin is caused to react with carbon monoxide in the presence of a strongly acidic catalyst such as $H_2SO_4$, $H_2SO_4$—$BF_3$, $H_3PO_4$—$BF_3$ or $BF_3$—$H_2O$ at elevated temperature and high pressure, see British patents Nos. 798,065 and 883,243 issued to Studien-Gesell. Kohle, published on July 19, 1958 and Nov. 29, 1961 respectively. The overall reaction of such process involves the combination of one mole of olefinic feedstock with one mole of water and one mole of carbon monoxide to provide the carboxylic acid product having one more carbon atom than the olefin feedstock. In carrying out this process in two steps, the first step involved reaction of the olefinic compound with carbon monoxide and, e.g., a hydrated boron fluoride catalyst corresponding approximately to $BF_3.2H_2O$. An exothermic reaction occurs with the formation of what may be called a complex of the hydrated boron fluoride catalyst, the carbon monoxide, and the olefin. In the second step of the two-step process, it is then necessary to hydrolyze this complex using about one mole of water per mole of carbon monoxide complexed. Improvements in the hydrolysis are described in U.S. Pat. Nos.3,262,954 and 3,296,286 to Wehe et al., issued on July 26, 1966 and Jan. 3, 1967, respectively. All of the foregoing patents of the prior art are incorporated herein by reference.

It has also been proposed to use a catalyst consisting of concentrated sulfuric acid and a copper (I) compound in carrying out at a low temperature and low pressure the synthesis of a carboxylic acid starting from an olefin or alcohol and carbon monoxide, but such proposal has the disadvantage that at a reaction temperature of 45° C. or higher, the yield of carboxylic acid decreases rapidly and at 50° C. almost no carboxylic acid is formed. Moreover, it is difficult to separate the carboxylic acids from the catalyst.

Up to the present time, copper carbonyl solutions have been prepared by causing a copper (I) compound to absorb carbon monoxide in the presence of a solvent, but, in general, only 1 mol or less of carbon monoxide is absorbed per 1 mol of copper (I). It has recently been reported in Nikkashi" (J. Chem. Soc. Japan, Pure Chem. Sect.) 91, 625 (1970) that when sulfuric acid is present in a high concentration in the process of reacting a copper (I) compound with carbon monoxide, the ratio of CO/Cu (I) reaches 1.0–3.0 mol/mol at a low temperature under pressure. However, there has been no disclosure in the literature of a ratio exceeding 3.0 mol/mol.

The catalytic compositions of the present invention are especially suited for the preparation of tertiary acids, i.e., those containing a tertiary carbon atom which is attached by its remaining bond to a carboxyl group, also called neo acids. The product acids have utility in agriculture, e.g., as fungicides — see British patent No. 1,037,761 to the duPont Company, published on Aug. 3, 1966, which is incorporated herein by reference; and also have utility in preparing paint driers and peroxides which are chemical initiators, such driers peroxy pivalates.

SUMMARY OF THE INVENTION

It has now been found that a superior catalyst for treating olefins or alcohols with carbon monoxide in the preparation of carboxylic acids, comprises a copper carbonylhydrated boron trifluoride solution. In this context the term "hydrated boron trifluoride" means a hydrate of boron trifluoride, or a mixture of hydrates, or a solution of a hydrate in excess water. In this system the copper carbonyl acts as a co-catalyst to improve the effectiveness of the hydrated boron trifluoride and increase the selectivity to carboxylic acids. If desired a mineral acid, preferably sulfuric acid, phosphoric acid or hydrogen fluoride, is included and the amount of the more costly and difficult to handle boron trifluoride gas is thereby reduced while the reaction rate and selectivity can be maintained substantially constant.

The catalyst solutions may be prepared by causing a copper (I) compound to react with carbon monoxide in the presence of hydrated boron trifluoride and, if desired, a mineral acid. The choice of copper (I) compound is not particularly limited but it must be a compound capable of forming a copper (I) carbonyl through the reaction with carbon monoxide in hydrated boron trifluoride; preferred is copper (I) oxide. The copper (I) carbonyl may be prepared in situ in the reactor or it may be preformed.

The olefins and alcohols used as a raw material in the process of the invention are aliphatic olefins having three or more carbon atoms, alicyclic olefins, and alicylclic and aromatic compounds each having a substituent of aliphatic olefin, and alcohols corresponding to these compounds, for example, propylene, n-butylene, i-butylene, pentene, hexene, dodecene, cyclopentene, cyclohexene, isopropanol, n-butanol, sec-butanol, tert-butanol, pentanol, hexanol and cyclohexanol. Furthermore, hydrocarbon mixtures obtained in the petroleum refining or petrochemical industry may be used, for example, olefin-containing hydrocarbon mixtures which are generally called "$C_4$-fraction" or "$C_5$-fraction".

The reaction of such olefin or alcohol with carbon monoxide is carried out at a reaction temperature of from −20° to 150° C., generally, from 0° to 120° C., preferably from 10° to 50° C. The pressure of carbon monoxide may be atmospheric pressure, but it is desirable in view of the low solubility of carbon monoxide in the medium as well as the boiling point of the raw material to effect the reaction under a high pressure, so that 1 to 100 atmospheres, preferably from 1 to 20 atmospheres may be employed.

The hydrated boron trifluoride used for the practice of the invention is obtained by adding boron trifluoride to water and, in particular, it is preferred to use boron trifluoride hydrate(s) or an aqueous solution of a hydrate obtained by causing 1 mol of boron trifluoride to be absorbed in 1–3 mols of water. The use of water in a proportion of more than 3 mols to 1 mol of boron trifluoride should be avoided, since a part of the boron trifluoride decomposes to boric acid which is undesirable.

The reaction may be carried out in batchwise, semi-batchwise or continuous manner. Separation and reuse of the hydrated boron trifluoride can readily be accomplished in the process of the invention merely by allowing the reaction products to stand, if sufficient water has been provided initially to satisfy the stoichiometric requirements for releasing the carboxylic acids. On the other hand, it is also within the scope of this invention to carry out a separate second step of hydrolysis to obtain the carboxylic acids, as conventionally practiced in the Koch process. That is to say, after the first step has been carried out, the product acids can be caused to separate out by settling by adjusting the $H_2O:BF_3$ ratio to at least 2.0.

According to the invention, copper carbonyl can readily be produced having a CO/Cu(I) ratio of 1.0–4.0 mol/mol, the infrared absorption spectrum of which shows that a peak possibly corresponding to copper (I) monocarbonyl, that is, wave number 2168 $cm^{-1}$ decreases with the increase of CO/Cu(I) ratio, and instead a peak of wave number 2190 $cm^{-1}$ appears while the other peak disappears. From this phenomenon one can postulate the presence of copper (I) tetracarbonyl which has hitherto been unknown. The copper (I) carbonyl solution obtained by the process of the invention is suitable for use as a catalyst for various organic syntheses, in particular, of hydrocarbons or alcohols with carbon monoxide, for example, reactions of olefins or alcohols with carbon monoxide to produce carboxylic acids such as pivalic acid, reaction of methanol with carbon monoxide to produce acetic acid and reactions of olefins with water gas to synthesize aldehydes or alcohols.

BRIEF DESCRIPTION OF THE DRAWING

The FIG. is a series of infrared absorption spectra of a number of catalytic compositions in accordance with the invention in which the molar amount of CO absorbed per mole of copper (I) is varied.

PREFERRED EMBODIMENTS

The invention is illustrated by the following examples.

EXAMPLE 1

In a four-necked flask of 200 ml was charged 100 ml of aqueous boron trifluoride, the $H_2O:BF_3$ ratio of which was varied as shown in Table I, and then 5.0 g. (0.035 mol) of cuprous oxide was added thereto with agitation. The flask was evacuated, replaced by carbon monoxide and the replacement was repeated to form inside an atmosphere of carbon monoxide. Carbon monoxide was introduced into the flask at atmospheric pressure while the flask was held at a predetermined temperature (25° C.) until the absorption of carbon monoxide ceased. In this case, the quantity of absorption of carbon monoxide by copper depended on the concentration of boron trifluoride.

To the reaction solution in which carbon monoxide had been absorbed was added 16 g. (0.22 mol) of tert-butanol at a rate of 0.2 ml/min with stirring and the stirring was continued until the absorption of carbon monoxide ceased. After the reaction, the reaction solution separated into two layers. All the reaction products were poured into ice water, organic substances were separated and carboxylic acids were isolated therefrom in conventional manner, i.e., by an alkaline treatment, followed by titration and chromatography. The results are shown in Table I. At the same time, Comparative Experiments were carried out using a copper (I) compound-free aqueous boron trifluoride (Comparative Example 1), a solution of a copper (I) compound in 98% sulfuric acid (Comparative Example 2) and a solution of a copper (I) compound in 82% sulfuric acid (Comparative Example 3). As is apparent from Table I, the results of these Comparative Examples were inferior to those of the present invention, in particular with respect to the selectivity to carboxylic acids. In the case of $H_2O/BF_3 = 1.9$ (Experiment No.1), in particular, carbon monoxide was absorbed in 70 minutes until CO/Cu = 1.2, whilst in the case of using 82% sulfuric acid (Comparative Example 3) corresponding to $H_2O/BF_3 = 1.9$ in acid strength, that molar ratio reached only CO/Cu = 0.4 in 7 hours.

TABLE I

| Experiment No. | Properties of Aqueous Boron Trifluoride Solution | | | Conversion of tert-Butanol (mol %) | Selectivity of tert-Butanol to Carboxylic Acids (mol %) | Composition of Carboxylic Acids* in Product (%) | | |
|---|---|---|---|---|---|---|---|---|
| | $H_2O/BF_3$ (mol/mol) | $BF_3$ mol/100 ml | CO/Cu (mol/mol) | | | $C_5$- acids | $C_9$- acids | other acids |
| 1 | 1.9 | 1.59 | 1.2 | 67 | 6 | 4 | 40 | 56 |
| 2 | 1.7 | 1.68 | 1.4 | 78 | 55 | 6 | 60 | 34 |
| 3 | 1.5 | 1.76 | 1.7 | 80 | 71 | 22 | 45 | 35 |
| 4 | 1.3 | 1.86 | 2.2 | 83 | 85 | 42 | 22 | 36 |
| 5 | 1.05 | 2.00 | 3.0 | 82 | 94 | 40 | 21 | 39 |
| 6 (Comp. Ex.1) | 1.3 | 1.86 | Cu compound-free | 84 | 1 or less | — | — | — |
| 7 (Comp. Ex.2) | 98% $H_2SO_4$** | | 1.4 | 95 | 24 | 24 | 22 | 54 |
| 8 (Comp. Ex.3) | 82% $H_2SO_4$*** | | 0.4 | 74 | 1 or less | — | — | — |

*Carboxylic acids are all tertiary carboxylic acids.
**98% $H_2SO_4$ corresponds to $H_2O/BF_3 = 1.3$ in acid strength.
***82% $H_2SO_4$ corresponds to $H_2O/BF_3 = 1.9$ in acid strength.

EXAMPLE 2

This Example was carried out under the same conditions as those of Example 1, Experiment No. 4, except that the temperature was varied. The results obtained were as shown in Table II.

As is evident from Table II, the reaction could be completed even at a reaction temperature of 80° C. according to the invention.

TABLE II

| Experiment No. | Reaction Temp. (°C.) | Properties of Aqueous Boron Trifluoride Solution | | | Conversion of tert-Butanol (mol %) | Selectivity of tert-Butanol to Carboxylic acids (mol %) | Composition of Carboxylic Acids* in Product(%) | | |
|---|---|---|---|---|---|---|---|---|---|
| | | $H_2O/BF_3$ (mol/mol) | $BF_3$ mol/100 ml | CO/Cu (mol/mol) | | | $C_5$- acids | $C_9$- acids | other acids |
| 9 | 5 | 1.3 | 1.86 | 2.7 | 18 | 25 | 4 | 35 | 61 |
| 4 | 25 | 1.3 | 1.86 | 2.2 | 83 | 85 | 42 | 22 | 36 |
| 10 | 50 | 1.3 | 1.86 | 1.5 | 94 | 76 | 30 | 28 | 42 |
| 11 | 80 | 1.3 | 1.86 | 1.1 | 100 | 40 | 5 | 30 | 65 |

*Carboxylic acids are all tertiary carboxylic acids.

EXAMPLE 3

This Example was carried out under the same conditions as those of Example 2, Experiment No. 10 except that the $H_2O/BF_3$ (mol/mol) ratio was adjusted to 1.5 and various raw materials were used per the following Table III:

TABLE III

| Raw Material | Conversion (mol %) | Selectivity to Carboxylic Acids (mol %) |
|---|---|---|
| diisobutylene | 92 | 69 |
| cyclohexanol | 89 | 87 |
| cyclohexene | 91 | 76 |

EXAMPLE 4

100 ml (150 g) of aqueous boron trifluoride having a $H_2O/BF_3$ (mol/mol) ratio of 2.7, 5.0 g (0.035 mol) of cuprous oxide and 21.3 g (0.187 mol) of diisobutylene were charged to a tantalum autoclave of 300 ml, into which carbon monoxide was then forcibly introduced under a pressure of 60 kg/cm². After stirring at room temperature for 30 minutes, the pressure decreased to 50 kg/cm². Then the autoclave was heated at 80° C. for 4 hours. The carboxylic acids were obtained from the reaction products as described in Example 1 and analysis gave the following results:

Conversion of diisobutylene = 86%
Selectivity to carboxylic acids = 85%

Distribution of carboxylic acids $C_5$ - acid = 48.0%
$C_9$ - acid = 43.5%
other acids = 8.5%

EXAMPLE 5

To a four-necked flask of 100 ml, which had been evacuated and replaced by carbon monoxide repeatedly to form an atmosphere of carbon monoxide inside, were charged 50 ml of a mixture of phosphoric acid, boron trifluoride and water in a proportion of 1 mol : 4.7 mols : 6 mols and 0.715 g (5 millimol) of cuprous oxide. Carbon monoxide was introduced with adequate agitation into the flask at atmospheric pressure while the charged materials were held at a predetermined temperature until the absorption of carbon monoxide ceased.

To the flask was added 7.4 g (0.1 mol) of tert-butanol with stirring under 1 atmosphere of carbon monoxide at a rate of 0.1 ml/min. and the stirring was further continued until the absorption of carbon monoxide ceased. The reaction products were poured into ice water. Separation and analysis of carboxylic acids were as described in Example 1. The results are shown in Table IV.

Similar procedures were repeated with a catalyst consisting of 50 ml of a mixture of phosphoric acid, boron trifluoride and water in a molar proportion of 1 : 1 : 1 and 0.715 g of cuprous oxide to obtain the results as shown in Table IV.

Comparative Examples were carried out using a copper (I) compound-free mixture of phosphoric acid, boron trifluoride and water in a molar ratio of 1 : 4.7 : 6 (Comparative Example 4), 50 ml of a solution of phosphoric acid and water in a molar ratio of 1 : 1.2 and 0.715 g of cuprous oxide (Comparative Example 5) and a copper (I) compound-free solution of phosphoric acid and water in a molar ratio of 1 : 1.2 (Comparative Example 6). The results of these Comparative Examples were greatly inferior to those of the present invention, in particular with respect to the selectivity to carboxylic acids.

As is evident from Table IV, when phosphoric acid is employed, the content of boron trifluoride can be reduced while conversion is maintained substantially constant and selectivity is increased in comparison with Experiment No.19 (Comparative Example 7) in which boron trifluoride and water in a molar ratio of 1.0 : 1.5 and a copper compound are used. This means that a part of the boron trifluoride can be replaced by a less expensive mineral acid such as phosphoric acid.

Moreover, carbon monoxide was caused to be absorbed in a solution consisting of phosphoric acid, boron trifluoride and water in a molar ratio of 1 : 4.7 : 6 and cuprous oxide and the quantity of absorption of CO was measured to obtain the results: 1.2 mols at 53° C., 2.0 mols at 20° C., 3.0 mols at −3° C. and 3.9 mols at −40° C. per 1 mol of copper (I). It can be theorized from these results that copper (I) tetracarbonyl was present.

TABLE IV

| Experiment No. | Properties of Aqueous Phosphoric Acid & Boron Trifluoride Solution | | | | | Reaction Temperature(°C) | Conversion of tert-Butanol (mol%) | Selectivity of tert-Butanol to Carboxylic Acids (mol%) | Composition of Carboxylic acids***** in Product (%) | | |
|---|---|---|---|---|---|---|---|---|---|---|---|
| | $H_3PO_4/BF_3/H_2O$ (mol ratio) | | | $BF_3$ content (wt.%) | Cuprous oxide (milli- mol/100 ml) | CO/Cu (mol/mol) | | | | $C_5$- acids | $C_9$- acids | other acids |
| 12 | 1.0 | 4.7 | 6.0 | 69.1 | 10 | 1.81 | 25 | 72 | 98 | 64 | 19 | 17 |
| 13 | 1.0 | 4.7 | 6.0 | 69.1 | 10 | 1.47 | 40 | 87 | 98 | 71 | 8 | 21 |
| 14 | 1.0 | 4.7 | 6.0 | 69.1 | 10 | 1.26 | 50 | 93 | 83 | 43 | 18 | 39 |
| 15 | 1.0 | 1.0 | 1.0 | 36.9 | 10 | 1.41 | 25 | 78 | 80 | 28 | 39 | 33 |
| 16 | 1.0 | 4.7 | 6.0 | 69.1 | — | — | 25 | 84 | 4 | 18 | 27 | 55 |
| 17 | 1.0 | — | 1.2 | — | 10 | 1.00 | 25 | 65 | 1 or less | — | — | — |
| 18 | 1.0 | — | 1.2 | — | — | — | 25 | 68 | 1 or less | — | — | 58 — |

TABLE IV-continued

| Experiment No. | Properties of Aqueous Phosphoric Acid & Boron Trifluoride Solution | | | | Reaction Temperature (°C) | Conversion of tert-Butanol (mol%) | Selectivity of tert-Butanol to Carboxylic Acids (mol%) | Composition of Carboxylic acids***** in Product (%) | | |
|---|---|---|---|---|---|---|---|---|---|---|
| | $H_3PO_4/BF_3/H_2O$ (mol ratio) | $BF_3$ content (wt.%) | Cuprous oxide (milli-mol/100 ml) | CO/Cu (mol/mol) | | | | $C_5$-acids | $C_9$-acids | other acids |
| 19 | — 1.0 1.5 | 71.5 | 35 | 1.70 | 25 | 80 | 71 | 22 | 45 | 35 |

Comparitive Example 4
**Comparitive Example 5
***Comparative Example 6
****Comparative Example 7
*****Tertiary Carboxylic Acids

EXAMPLE 6

In a manner similar to that of Example 5, experiments employing tert-butanol were carried out using 50 mol of a mixture consisting of sulfuric acid, boron trifluoride and water in a molar ratio of 1 : 1 : 1.5 and 0.715 g of cuprous oxide to obtain the results as shown in Table V. Comparative Examples were carried out using a cuprous oxide-free mixture of sulfuric acid, boron trifluoride and water (Comparative Example 8), a solution of cuprous oxide in 98% sulfuric acid (Comparative Example 9) and cuprous oxide-free 98% sulfuric acid (Comparative Example 10). The results of these Comparative Examples were greatly inferior to those of the present invention, in particular with respect to the selectivity to carboxylic acids.

It is apparent from these results that the conversion is hardly changed and selectivity is improved even though the content of boron trifluoride in the solution is lower than in Comparative Example 7 of Table IV.

EXAMPLE 7

In a manner similar to that of Example 5, experiments employing tert-butanol were carried out using 50 ml of a mixture consisting of hydrogen fluoride, boron trifluoride and water in a molar ratio of 1 : 1 : 1.44 and 0.715 g of cuprous oxide to obtain the results as shown in Table VI. Comparative Examples were carried out using a cuprous oxide-free mixture of hydrogen fluoride, boron trifluoride and water (Comparative Example 11), and a cuprous oxide-free solution of hydrogen fluoride and water in a molar ratio of 1 : 1 (Comparative Example 12). The results of these Comparative Examples were greatly inferior to those of the present invention, in particular with respect to the selectivity to carboxylic acids.

It is apparent from these results that the conversion and selectivity are improved even though the content of boron trifluoride in the solution is lower than in Comparative Example 7 of Table IV.

TABLE VI

| Experiment No. | Properties of Aqueous Hydrogen Fluoride & Boron Trifluoride Solution | | | | Reaction Temperature (°C) | Conversion of tert-Butanol (mol %) | Selectivity of tert-Butanol to Carboxylic Acids (mol%) | Composition of Carboxylic Acids*** in Product (%) | | |
|---|---|---|---|---|---|---|---|---|---|---|
| | $HF/BF_3/H_2O$ (mol ratio) | $BF_3$ content (wt.%) | Cuprous oxide (milli-mol/100 ml) | CO/Cu (mol/mol) | | | | $C_5$-acids | $C_9$-acids | other acids |
| 25 | 1.0 1.0 1.44 | 59.6 | 10 | 1.80 | 25 | 94 | 99 | 81 | 10 | 9 |
| 26 | 1.0 1.0 1.44 | 59.6 | — | — | 25 | 95 | 1 or less | — | — | — |
| 27 | 1.0 — 1.0 | — | — | — | 25 | 72 | 1 or less | — | — | — |

*Comparative Example 11
**Comparative Example 12
***Tertiary Carboxylic Acids

EXAMPLE 8

This Example was carried out under the same conditions as those of Example 5, Experiment No. 13 but using various raw materials as shown in the following Table VII in place of the tert-butanol. The results are tabulated below:

TABLE V

| Experiment No. | Properties of Aqueous Sulfuric Acid and Boron Trifluoride Solution | | | | Reaction Temperature (°C) | Conversion of tert-Butanol (mol %) | Selectivity of tert-Butanol to Carboxylic Acids (mol %) | Composition of Carboxylic Acids**** in Product (%) | | |
|---|---|---|---|---|---|---|---|---|---|---|
| | $H_2SO_4/BF_3/H_2O$ (mol ratio) | $BF_3$ content (wt.%) | Cuprous oxide (milli-mol/100 ml) | CO/Cu (mol/mol) | | | | $C_5$-acids | $C_9$-acids | other acids |
| 20 | 1.0 1.0 1.5 | 35.2 | 10 | 1.35 | 25 | 78 | 79 | 50 | 16 | 34 |
| 21 | 1.0 1.0 1.5 | 35.2 | 10 | 1.75 | 0 | 92 | 87 | 52 | 23 | 25 |
| 22* | 1.0 1.0 1.5 | 35.2 | — | — | 25 | 80 | 1 or less | — | — | — |
| 23** | 98 % $H_2SO_4$ | — | 35 | 1.40 | 25 | 95 | 24 | 24 | 22 | 54 |
| 24*** | 98 % $H_2SO_4$ | — | — | — | 25 | 93 | 1 or less | — | — | — |

*Comparative Example 8
**Comparative Example 9
***Comparative Example 10
****Tertiary Carboxylic Acid

TABLE VII

| Raw Material | Conversion (mol %) | Selectivity to Carboxylic Acids (mol %) |
|---|---|---|
| diisobutylene | 93 | 65 |
| cyclohexene | 88 | 70 |

EXAMPLE 9

80 ml of a mixture of phosphoric acid, boron trifluoride and water in a molar ratio of 1 : 4.7 : 6 and 0.715 g of cuprous oxide were charged to a glass-lined autoclave of 300 ml, stirred at 30° C. under 30 kg/cm² of carbon monoxide for 30 minutes and then 34 g (0.3 mol) of diisobutylene was introduced thereinto, followed by reaction for a period of 30 minutes. The reaction products were poured into ice water. Separation and analysis of carboxylic acids were as described in Example 1. The following results were obtained:

Conversion of diisobutylene = 99 mol %
Selectivity to carboxylic acids = 99%

Distribution of carboxylic acids $C_5$-acids = 81%
$C_9$-acids = 16%
other acids = 3%

EXAMPLE 10

50 ml of hydrated boron trifluoride, of which the ratio of boron trifluoride to water was varied as shown in the following Table, and 0.715 g (5 millimol) of cuprous oxide were charged to a four-necked flask of 100 ml, maintained under vacuum by means of a vacuum pump, kept at a predetermined temperature and, with adequate agitation, carbon monoxide was introduced at 1 atmosphere into the flask from a gas burette until the absorption of carbon monoxide ceased. The amount of absorption of carbon monoxide was measured, converted into the volume at 0° C. and the molar amount of carbon monoxide was calculated per 1 mol of copper (I) as shown in Table VIII. As is evident from this Table, in the system where there are 2.50 mols or more of water per 1 mol of boron trifluoride, the ratio of CO/Cu (I) does not exceed 1.00 mol/mol at 0° C. or higher, while in the case of less than 2.50 mols of water, it exceeds 1.00 mol/mol at any temperature, for example, in the case of 1.09 moles of water, 3.00 mol/mol at 19° C. and 4.00 mol/mol at −10° C. These results may indicate the presence of copper (I) tetracarbonyl.

Infrared spectroscopy measurements were made on the resulting solutions of copper (I) carbonyls having a CO/Cu(I) ratio of 1.0, 2.0, 3.0, 3.25, and 3.7 mol/mol respectively, giving infrared absorption spectra as shown in the figure. When CO/Cu(I) ratio = 1.0, only a peak of wave number 2168 cm⁻¹ appears, but when CO/Cu(I) ratio = 2.0, another peak of wave number 2190 cm⁻¹ appears and gradually replaces the former peak with increase of the CO/Cu(I) ratio. It can be postulated from this result that copper (I) tetracarbonyl is formed in hydrated boron trifluoride and that the quantity thereof varies with the temperature.

TABLE VIII

| Experiment No. | $BF_3/H_2O$ ratio (mol/mol) | CO/Cu(I) ratio (mol/mol) | | | | | | | | |
|---|---|---|---|---|---|---|---|---|---|---|
| | | 60° C. | 50° C. | 40° C. | 30° C. | 20° C. | 10° C. | 0° C. | −10° C. | −20° C. |
| 28 | 1.0   2.50 | 1.00 | 1.00 | 1.00 | 1.00 | 1.00 | 1.00 | 1.00 | 1.02 | — |
| 29 | 1.0   2.00 | 1.04 | 1.09 | 1.14 | 1.20 | 1.28 | 1.42 | 1.61 | 1.74 (−6° C.) | — |
| 30 | 1.0   1.50 | 1.14 | 1.26 | 1.40 | 1.60 | 1.83 | 2.14 | 2.50 | 2.79 (−6° C.) | — |
| 31 | 1.0   1.26 | — | — | 2.05 (33° C.) | 2.11 | 2.43 | 2.80 | 3.20 | 3.45 (−6° C.) | |
| 32 | 1.0   1.13 | — | — | — | 2.42 (26° C.) | 2.62 | 3.05 | 3.50 | 3.83 | 4.00 |
| 33 | 1.0   1.09 | — | — | — | — | 3.23 (14° C.) | 3.40 | 3.75 | 4.00 | 4.00 |

EXAMPLE 11

Using 50 ml of a mixture consisting of hydrated boron trifluoride and phosphoric acid in place of 50 ml of hydrated boron trifluoride in Example 10, carbon monoxide was absorbed in cuprous oxide in a manner similar to that of Example 10 and the quantity of absorption was measured to obtain the results as shown in Table IX. The infrared absorption spectrum of the product was measured by the same method as that of Example 10 and similar spectra were obtained.

TABLE IX

| Experiment No. | $H_3PO_4BF_3/H_2O$ ratio (mol/mol/mol) | CO/Cu(I) ratio (mol/mol) | | | | | | | | | |
|---|---|---|---|---|---|---|---|---|---|---|---|
| | | 60° C. | 50° C. | 40° C. | 30° C. | 20° C. | 10° C. | 0° C. | −10° C. | −20° C. | −30° C. |
| 34 | 1.0   4.7   6.0 | 1.23 (53° C.) | 1.27 | 1.44 | 1.68 | 2.00 | 2.43 | 2.88 | 3.32 | 3.56 | 3.88 |
| 35 | 1.0   1.66   0.96 | — | 1.56 (48° C.) | 1.76 | 2.03 | 2.36 | 2.75 | 3.20 | 3.70 | — | — |
| 36 | 1.0   1.0   1.0 | 1.02 | 1.09 | 1.20 | 1.33 | 1.52 | 1.76 | 2.08 | 2.50 | 3.04 | — |

EXAMPLE 12

Using 50 ml of a mixture consisting of boron trifluoride, sulfuric acid and water in a molar ratio of 4.6 : 1.0 : 5.2 in place of 50 ml of hydrated boron trifluoride in Example 10, carbon monoxide was absorbed in cuprous oxide at −6° C. in a manner similar to that to Example 10, to obtain at CO/Cu(I) ratio of 3.2 mol/mol.

EXAMPLE 13

Using 50 ml of a mixture consisting of boron tri fluoride, hydrofluoric acid and water in a molar ratio of 1.0 : 1.0 : 1.44 in place of 50 ml of hydrated boron trifluoride in Example 10, carbon monoxide was absorbed in cuprous oxide at 18° and −1° C. in a manner similar to that of Example 10, to obtain a CO/Cu(I) ratio of 2.0 mol/mol in each case.

EXAMPLE 14

The utility of the copper carbonyl obtained is illustrated by the following preparation of carboxylic acids. Into 100 ml of a solution comprising hydrated boron trifluoride and having a CO/Cu(I) ratio of 2.27 mol/mol obtained by absorption of carbon monoxide at 25° C. (Example 10, Experiment No.31) was further bubbled carbon monoxide at 25° C. with adequate agitation and 16 g (0.22 mol) of tert-butanol was added at a rate of 0.2 ml/min and reacted. The reaction products were poured into ice water and the carboxylic acids were isolated as described in Example 1 and analyzed by gas chromatography. The following results were obtained:

Conversion of tert-butanol: 83 mol %

Selectivity of tert-butanol to carboxylic acid: 99 mol %

Distribution of carboxylic acid (tertiary) in the Product: $C_5$ acids 70 mol %, $C_9$ acids 17 mol % and other acids 13 mol %.

What is claimed is:

1. A catalyst composition useful for the treatment of olefins or alcohols with carbon monoxide in the preparation of carboxylic acids which consists essentially of a solution of hydrated boron trifluoride having a ratio of not more than 3 moles of water per mole of boron trifluoride and a minor amount of copper (I) carbonyl.

2. The catalytic solution of claim 1 wherein said copper carbonyl contains copper (I) tetracarbonyl.

3. The catalytic solution of claim 1 which further includes a mineral acid in a molar amount equal to or less than the molar amount of boron trifluoride.

4. The catalytic solution of claim 1 which further includes an acid selected from the group consisting of phosphoric acid, sulfuric acid, hydrogen fluoride, and mixtures thereof in a molar amount equal to or less than the molar amount of boron trifluoride.

5. A process which consists essentially of reacting a minor amount of a copper (I) compound capable of forming a copper (I) carbonyl, with carbon monoxide in the presence of hydrated boron trifluoride having a ratio of not more than 3 moles of water per mole of boron trifluoride.

6. A process as claimed in claim 5 wherein a mineral acid is included in the reactant mixture in a molar amount equal to or less than the molar amount of boron trifluoride.

7. A process as claimed in claim 5 wherein an acid selected from the group consisting of phosphoric acid, sulfuric acid, hydrogen fluoride, and mixtures thereof, is included in the reactant mixture in a molar amount equal to or less than the molar amount of boron trifluoride.

* * * * *